United States Patent [19]
Xanthakos et al.

[11] Patent Number: 5,183,465
[45] Date of Patent: Feb. 2, 1993

[54] APPARATUS FOR SUPPORTING AND MOVING NEEDLES AND TROCARS FOR PENETRATING THE ABDOMEN

[76] Inventors: Dimitrios Xanthakos, 6811 Hickory Hill Ct., Maumee, Ohio 43537; Gus Sevastakis, 5645 Angola Road, Toledo, Ohio 43615

[21] Appl. No.: 636,063

[22] Filed: Dec. 28, 1990

[51] Int. Cl.$^5$ ............................................. A61M 29/00
[52] U.S. Cl. .................................. 604/108; 604/106; 604/109; 604/117; 606/172
[58] Field of Search ............... 606/172, 173, 108, 198; 604/115, 117, 174–175, 177–178, 104–109, 106

[56] References Cited

U.S. PATENT DOCUMENTS

| | | | |
|---|---|---|---|
| 972,983 | 10/1910 | Arthur | 606/198 |
| 1,328,624 | 1/1920 | Graham | 604/108 |
| 3,717,151 | 2/1973 | Collett | 604/106 |
| 4,608,965 | 9/1986 | Anspach, Jr. et al. | 604/105 |
| 4,805,634 | 2/1986 | Ullrich et al. | 606/198 |

Primary Examiner—C. Fred Rosenbaum
Assistant Examiner—Ronald Stright, Jr.
Attorney, Agent, or Firm—Barnes, Kisselle, Raisch, Choate, Whittemore & Hulbert

[57] ABSTRACT

An apparatus is provided for supporting a Verres needle which includes a mechanism for grasping a portion of the abdomen such that the needle may be moved to penetrate the abdomen to create a space between the abdominal wall and the abdominal organs and includes a mechanism for advancing the Verres needle toward the abdominal cavity by relative movement to the needle with respect to the portion of the apparatus which holds the needle. The apparatus further includes a mechanism for controlling the movement of the needle relative to the grasping portion of the apparatus.

6 Claims, 4 Drawing Sheets

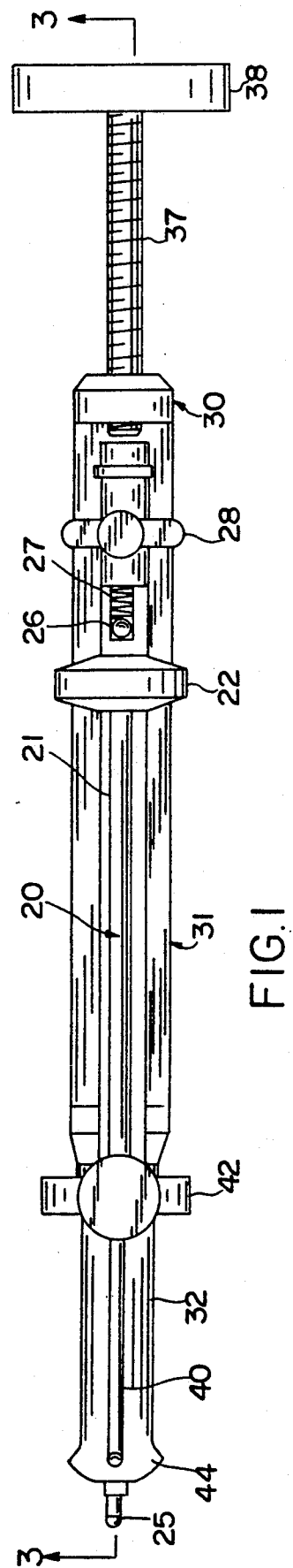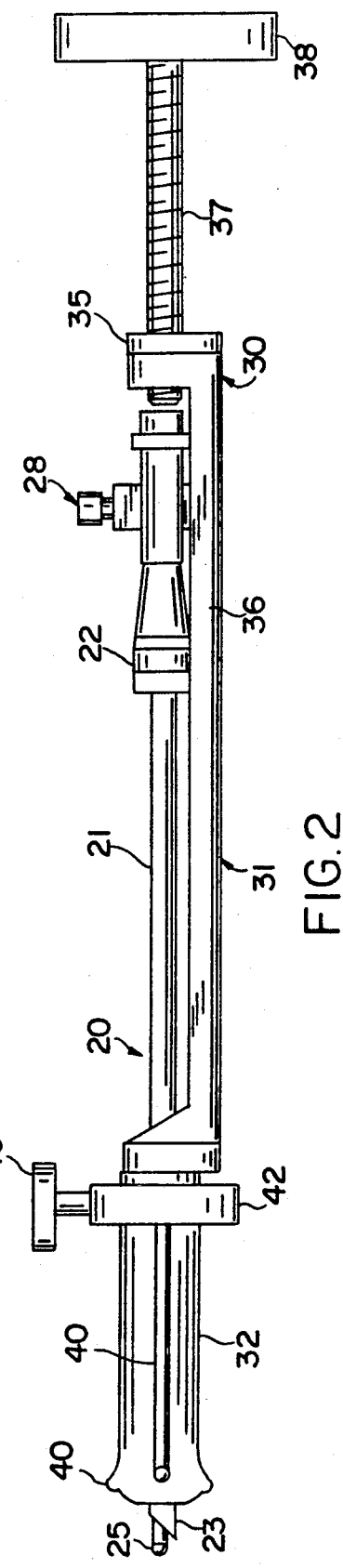

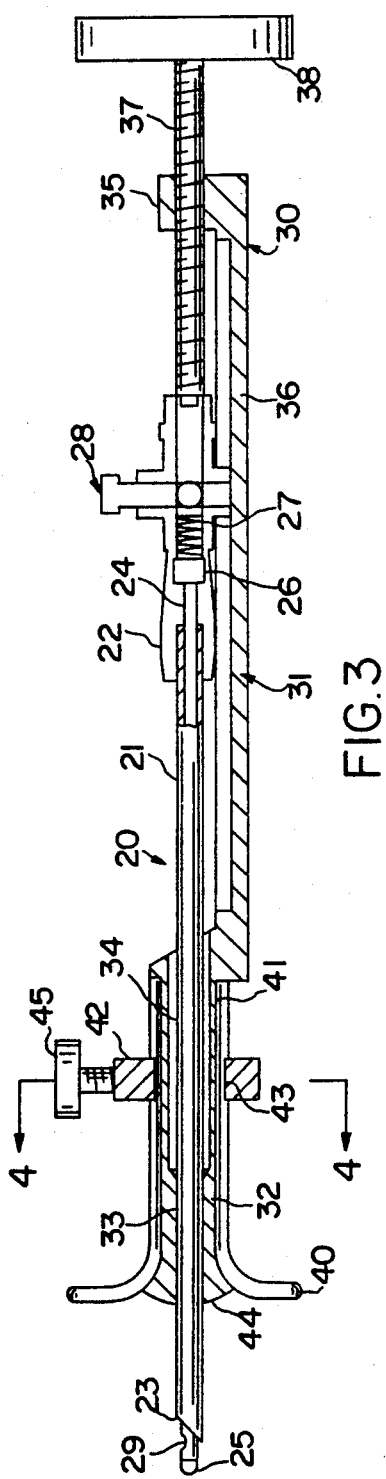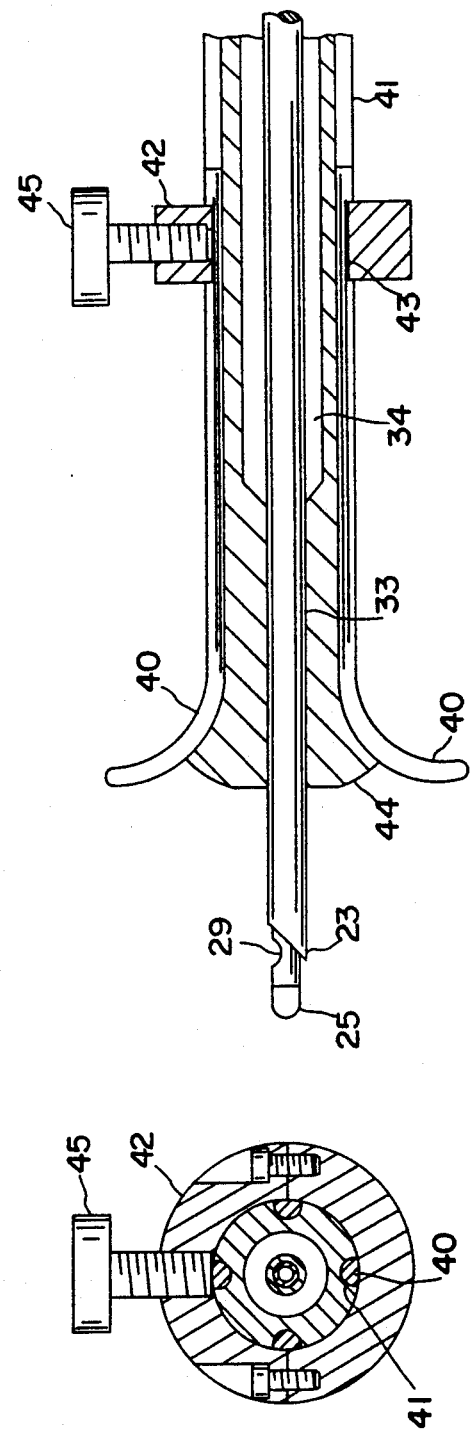
FIG. 3
FIG. 5
FIG. 4

APPARATUS FOR SUPPORTING AND MOVING NEEDLES AND TROCARS FOR PENETRATING THE ABDOMEN

This invention relates to the use of Verres needles and trocars in laparoscopy for penetrating the abdomen and particularly to an apparatus for supporting and moving needles and trocars for penetrating the abdomen.

BACKGROUND AND SUMMARY OF THE INVENTION

In abdominal surgery using laparoscopic techniques, the abdomen is initially penetrated with a needle, known as a Verres needle and carbon dioxide is utilized to extend the abdomen so that subsequent surgical steps can proceed.

The double-lumen Verres needle with its blunted spring-loaded mechanism is designed to allow a sharp penetration of the abdominal wall, yet protect the intra-abdominal viscera. It includes an outer sleeve with a sharp tip which harbors a blunt inner needle that is yieldingly urged outwardly of the outer sleeve by a spring. The manual pressure against the abdominal wall or peritoneum causes the blunt inner needle to retract, leaving the sharp outer sleeve unguarded to penetrate the abdominal layers. Once the resistance is overcome, the inner blunt needle springs out again, preventing any further damage to the intra-abdominal viscera by the sharp edge.

In many patients with strong abdominal tissues, greater force is required to penetrate the abdominal wall and the needle may be accidentally advanced deeper after its penetration of the peritoneum and may injure the bowel or major intra-abdominal vessels.

Injuries of the bowel and rarely of the major abdominal arteries or veins have been reported. Those injuries often required a major surgical exploration in order that they may be repaired and may even cause the death of patient if they go unnoticed.

To reduce the chance of injuries to the intra-abdominal organs, the abdominal wall is manually elevated by skin traction prior to manual insertion of the Verres needle. This elevation of the abdominal wall results in an increase of the distance of the abdominal wall from the major vessels and bowels. The insertion of the needle is facilitated by incising the skin with a scalpel to an opening of 3-4 mm.

The abdominal wall is elevated by grasping the peniculus with one hand or towel clips while the other hand directs the Verres needle at a right angle to the fascia and peritoneum and slowly penetrate the abdominal wall layers.

An experienced laparoscopist will notice a distinctive sensation when the needle transverses each of the layers of an abdominal wall and he will stop applying pressure after the needle has penetrated the peritoneum and he will be very cautious when piercing the peritoneum.

Among the objectives of the present invention are to provide an apparatus for holding the Verres needle and elevating the abdominal wall; which permits controlling the speed and force of insertion of the needle when piercing the abdominal wall; which can be sterilized and used repeatedly.

In accordance with the invention, an apparatus is provided for supporting a Verres needle which includes means for grasping a portion of the abdomen such that the needle may be moved to penetrate the abdomen to create a space between the abdominal wall and the abdominal organs and includes means for advancing the Verres needle toward the abdominal cavity by relative movement to the needle with respect to the portion of the apparatus which holds the needle. The apparatus further includes means for controlling the movement of the needle relative to the grasping portion of the apparatus.

DESCRIPTION OF THE DRAWINGS

FIG. 1 is a plan view of the apparatus embodying the invention.

FIG. 2 is a front elevational view of FIG. 1.

FIG. 3 is a sectional view taken along the line 3—3 in FIG. 1 showing the parts in a different operative position.

FIG. 4 is an enlarged sectional view taken along the line 4—4 in FIG. 3.

FIG. 5 is an enlarged fragmentary sectional view of a portion of FIG. 3.

DESCRIPTION

Figure 6:
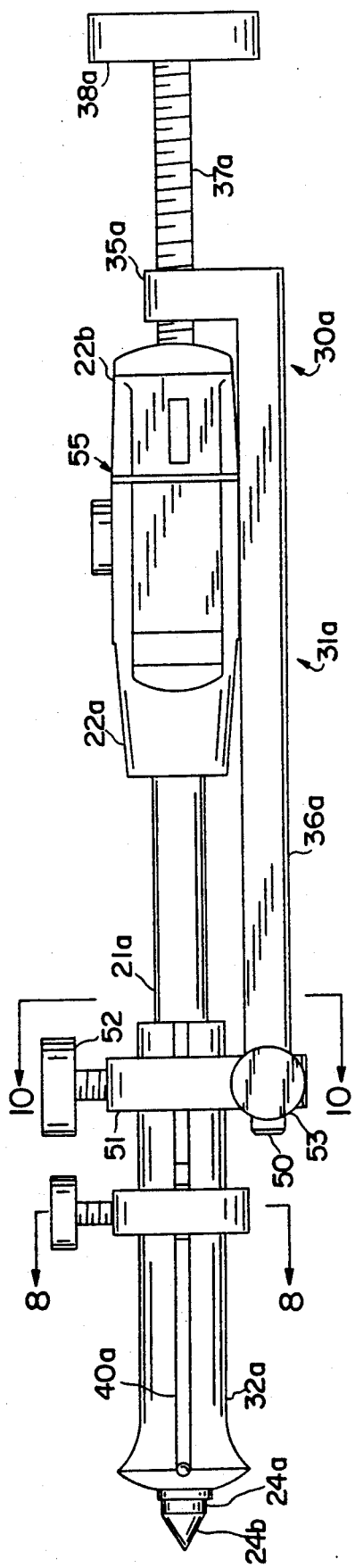
FIG. 6 is a front elevational view of a modified form of apparatus for use with a trocar.
Figure 7:
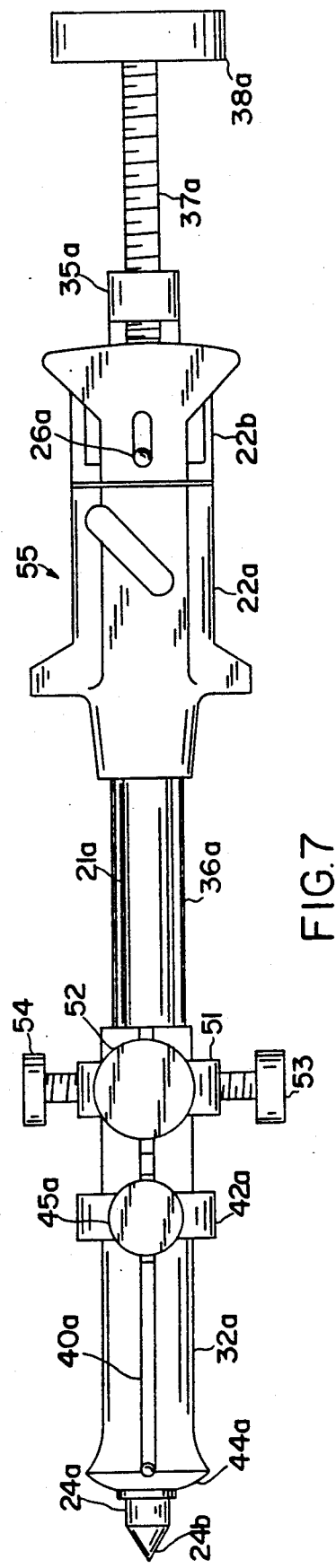
FIG. 7 is a plan view of the apparatus shown in FIG. 6.

Referring to FIG. 3, the apparatus embodying the invention is intended for use with a device 20 known as a Verres needle that is utilized in laparoscopy. The Verres needle 20 is well known in the art and comprises an outer sleeve 21 that is fixed at one end in a handle 22 and has an inclined sharp end 23 at the other end. The needle 20 further includes an inner needle 24 that has a blunt end 25 at one end and an enlarged end 26 at the other whereby it is yieldingly urged by a spring 27 axially outwardly relative to the outer sleeve 21. The Verres needle further includes a valve 28 which can be connected to a source of carbon dioxide gas for transmitting gas through the inner needle 24. Inner needle 24 has an opening 29 for passage of the carbon dioxide.

Referring to FIGS. 1-5, in accordance invention, the apparatus 30 comprises a body 31 which has an enlarged portion or head 32 at the outer end, the periphery of which includes means for grasping the abdominal wall, as presently described. The enlarged portion 32 includes a passage 33 for guiding the free end of the outer sleeve 21 of the Verres needle 20 and an enlarged opening 34 to facilitate insertion of the Verres needle 20. The body 31 includes an enlarged portion 35 at its other end connected by an integral wall 36. A threaded shaft or screw 37 is threaded through the wall for engagement with the end of the Verres needle to advance the Verres needle axially relative to the body 31. A knob 38 is provided on the threaded shaft or screw 37 to facilitate rotation thereof.

The means for grasping the abdominal wall and lifting it relative to the abdominal viscera comprises a plurality of circumferentially spaced spring fingers 40 which are positioned in grooves 41 in the periphery of the enlarged portion 32 and are moved axially relative thereto by a split ring 42 to which they are fixed axially as by grooves 43 therein. The enlarged portion 32 has an outwardly flared periphery 44 and the ends of spring fingers 40 are preferably flared such that when the spring fingers 40 are moved axially outwardly relative to the head 32, they will flare outwardly against the spring force, which tends to return them to their normally straight position, into the abdominal wall, so that they will grasp the abdominal wall in a manner that when the apparatus 30 is moved outwardly, it lifts the abdominal wall away from the abdominal organs.

The entire apparatus 30 is formed of material that can be sterilized such as stainless steel.

The apparatus may be used in the following manner:

The laparoscopist makes a small incision in the skin deep enough to cut through the skin and the subcutaneous fat or muscle fascia depending on the location of insertion of the Verres needle. The Verres needle apparatus 30 is placed into the incision and the sliding ring 42 is moved forward to expand the hook-like wires into the subcutaneous fat or muscle.

When sufficient grasping of the abdominal wall is accomplished, the laparoscopist locks the sliding ring 42 with the screw 45 in relation to the head 32 and pulls the Verres apparatus 30 backward rearwardly elevating the abdominal wall and insuring that a space (or distance) is created between the abdominal wall and abdominal organs.

When this is accomplished, he then advances the Verres needle 20 towards the abdominal cavity through the sliding cavity of the Verres needle apparatus 30.

The Verres needle approaching the peritoneum will require greater force to penetrate it and more importantly this force must remain very steady on the forward movement of the needle in order to prevent uncontrollable advancement of the needle beyond the peritoneum.

Thus, the assembly is provided with the screw 37 by which the Verres needle 20 may be pushed slowly toward the abdominal cavity. With the slow motion control of the screw 37 and the force created by pulling backward the washer 42 on the holding device, the Verres needle 20 slowly pierces the peritoneum without a jarring movement avoiding in this way the advancement of the needle 20 deep in the peritoneal cavity where an accidental injury of the intra-abdominal organs can take place. The spring loaded blunt inner needle 24 of the Verres needle 20 indicates that the piercing through the abdominal wall is completed.

The laparoscopist then reverses the forward motion of the screw 37. He performs an aspiration and injection test with a syringe to insure that the Verres needle 20 has not entered the bowel or a vessel. He then connects the Verres needle 20 through an axial opening in the handle 22 to pressurized carbon dioxide system insufflating the gas through the needle 20 and inner needle 24 to the abdominal cavity to insure that the abdominal wall has been raised and the pneumoperitoneum is formed separating the abdominal organs from the abdominal wall.

The laparoscopist then removes the Verres needle 20 and inserts a trocar slowly through the the same incision or other location as the planned procedure requires. After the trocar has enter the abdominal cavity, it is removed leaving in place the trocar sleeve through which a laparoscope is inserted for examination of the abdominal cavity or instruments are inserted to perform laparoscopic surgery without the need to perform another larger incision.

The insertion of the trocar can be accomplished with a similar holder to penetrate the abdominal wall with slow motion and great controllable force when required. Trocars are utilized in laparoscopy for penetrating the abdomen and thereafter the muscle and peritoneum so that a probe of a camera or surgical tools can be inserted into the abdominal cavity for performing the various surgical procedures. A plurality of trocars may be simultaneously utilized in different portions of the abdomen including, in some instances, insertion in the same opening through which the Verres needle was inserted and the abdomen was inflated by the carbon dioxide. In some instances, a single trocar may be used depending upon the nature of the surgical procedure.

Referring to FIGS. 6-11, a similar apparatus for utilization in inserting a trocar in the abdomen, either through the same opening in which the Verres needle has been used or through other openings in the abdomen, is provided for grasping the abdomen and manipulating the trocar in substantially the same manner as manipulating the Verres needle.

A trocar 55 generally has a similar construction to that utilized in Verres needles including an outer sleeve 21a that is fixed to a first handle portion 22a and an inner member 24a having a cutting edge 24b. The inner member 24a is fixed to a second handle portion 22b which snaps into position onto the handle portion 22a. After the laparoscopist makes the initial incision and the instrument is utilized to penetrate the abdominal wall, muscle and peritoneum, the inner member 24a is removed and the head 35a is disconnected leaving the outer sleeve 21a in position with the head 32a fixed thereto to maintain the grasp on the abdominal wall so that the trocar can be readily manipulated for viewing and access to various organs in the abdomen.

In this form, corresponding reference numerals have been provided to the parts with the suffix "a".

Figure 10:
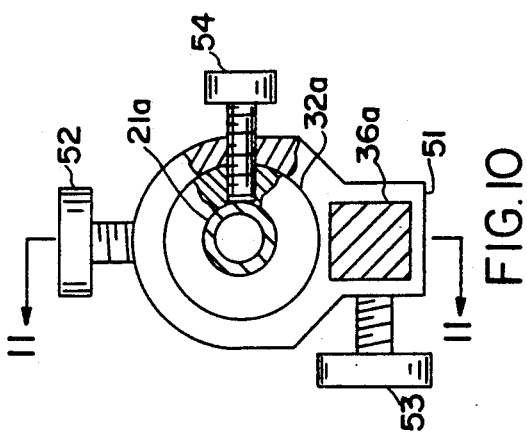
FIG. 10 is a sectional view taken along the line 10—10 in FIG. 6.

The apparatus differs in that the body 31a includes means for disconnecting the head 32a from the enlarged portion 35a. This is achieved by a projection 50 that extends into an opening in a collar 51 held in position by a screw 52 on the head 32a. A set screw 53 locks the portion 36a with the collar 51. As shown in FIG. 10, a set screw 54 extends through the head 32a into engagement with the outer sleeve 21a of the trocar to hold the outer sleeve in position with respect to the head 32a. This screw may be loosened to release the sleeve 21a so that a greater or lesser portion of the sleeve 21a can be provided within the abdomen relative to the head 32a.

In use, after the laparoscopist has inflated the abdomen by use of a Verres needle and the apparatus shown in FIGS. 1-5, the laparoscopist inserts the trocar 55 in the apparatus shown in FIGS. 6-11 and makes a small incision in the skin. The laparoscopist then utilizes the apparatus in the same manner to penetrate the inflated abdomen and grasp the abdominal wall. The laparoscopist then manipulates the trocar 55 by use of the screw 38a to penetrate the muscle and peritoneum. The inner member 24a is then removed leaving the trocar and the head in position for the various surgical procedures.

It can thus be seen that apparatus shown in FIGS. 6-11 permits the laparoscopist to grasp and move the abdominal wall as well as apply the substantial force required with the larger trocar needle through the muscle and peritoneum in a controlled fashion. As in the case of the apparatus for holding the Verres needle, the apparatus substantially decreases the risk of injury to abdominal organs obviating the problems that have heretofore been discussed with respect to control of the Verres needle.

Figure 12:
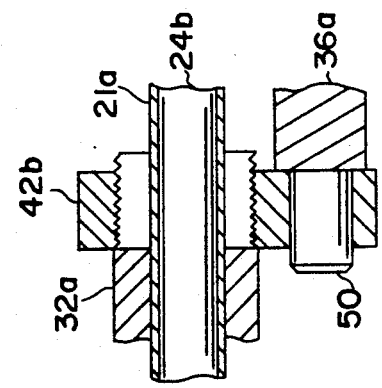
FIG. 12 is another sectional view similar to FIG. 11 showing a modified form of the apparatus.
Figure 9:
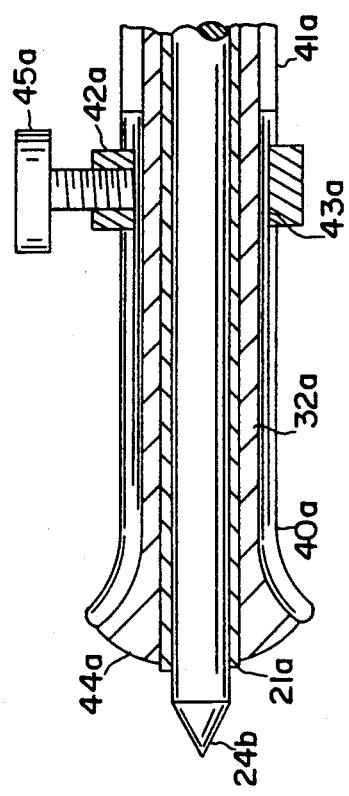
FIG. 9 is a fragmentary sectional view taken along the line 9—9 in FIG. 8.
Figure 11:
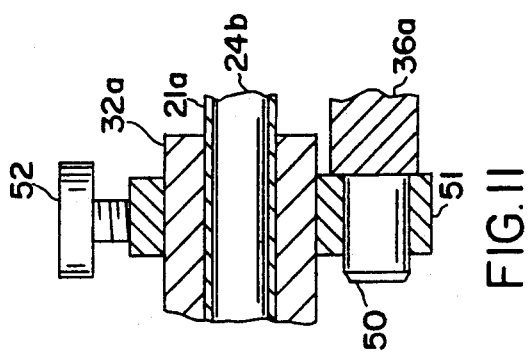
FIG. 11 is a sectional view taken along the line 11—11 in FIG. 10.
Figure 8:
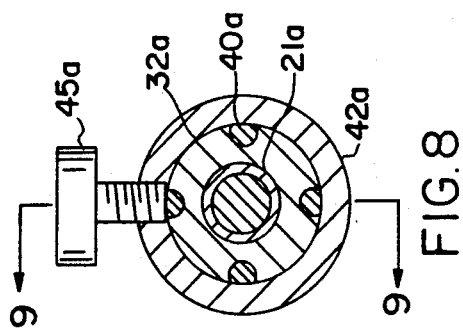
FIG. 8 is an enlarged sectional view taken along the line 8—8 in FIG. 6.

In the modified form shown in FIG. 12, the ring 42*b* is threaded on the enlarged head 32*a* rather than slideable, as in the forms shown in FIGS. 1-11.

We claim:

1. Apparatus for manipulating a Verres needle or trocar for use in laparoscopy comprising:

a body having an open portion for receiving and supporting a Verres needle or trocar, an enlarged portion at a distal end of said open portion, and an axial passage through said enlarged portion for axial movement of the Verres needle or trocar supported on said open portion, means at a proximal end of said body remote from said distal end for engaging the Verres needle or trocar supported on said open portion of said body and progressively advancing such Verres needle or trocar through said passage, and a plurality of resilient spring fingers disposed in a circumferential array on said enlarged portion of said body surrounding and parallel to said passage, flared means on said enlarged portion surrounding said passage at said distal end for engagement with said spring fingers, and means for moving said spring fingers axially along said enlarged portion simultaneously with each other against said flared means and independently of said engaging and advancing means so as to cam free ends of said spring fingers radially outwardly of said enlarged portion against resilient spring force of said spring fingers.

2. The apparatus set forth in claim 1 wherein said means for moving said spring fingers comprises a ring threaded on said enlarged body portion for advancing and retracting said fingers against said flared means.

3. The apparatus set forth in claim 1 wherein said means for moving said spring fingers comprises a slide member carried by and slidable on said enlarged body portion for advancing and retracting said fingers against said flared means.

4. The apparatus set forth in claim 3 including means for locking said slide member relative to said body.

5. The apparatus set forth in claim 1 including means removably disconnecting the enlarged portion of said body and said proximal end of said body.

6. The apparatus set forth in claim 5 including means on said enlarged portion for engaging the outer sleeve of a trocar for adjusting the length that a trocar projects beyond said enlarged portion of said body.

* * * * *